US011324618B2

(12) United States Patent
Wilger et al.

(10) Patent No.: US 11,324,618 B2
(45) Date of Patent: May 10, 2022

(54) DELIVERY SYSTEM FOR A PRELOADED FENESTRATED DEVICE HAVING A RATCHETED WIRE RELEASE

(71) Applicant: Cook Medical Technologies LLC, Bloomington, IN (US)

(72) Inventors: Kevin D. Wilger, Lafayette, IN (US); Jarin A. Kratzberg, Lafayette, IN (US); Brandon J. Davis, Fishers, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 15/903,478

(22) Filed: Feb. 23, 2018

(65) Prior Publication Data
US 2018/0243117 A1    Aug. 30, 2018

Related U.S. Application Data

(60) Provisional application No. 62/464,473, filed on Feb. 28, 2017.

(51) Int. Cl.
*A61F 2/966* (2013.01)
*A61F 2/07* (2013.01)
(Continued)

(52) U.S. Cl.
CPC .......... *A61F 2/966* (2013.01); *A61B 17/0218* (2013.01); *A61F 2/07* (2013.01);
(Continued)

(58) Field of Classification Search
CPC .. A61F 2/966; A61F 2/954; A61F 2/07; A61F 2002/9665; A61F 2002/9517;
(Continued)

(56) References Cited

U.S. PATENT DOCUMENTS 5,609,627 A    3/1997    Goicoechea et al.
5,662,703 A    9/1997    Yurek et al.
(Continued)

FOREIGN PATENT DOCUMENTS

EP    2 724 695    4/2014
EP    3 037 074    6/2016
(Continued)

OTHER PUBLICATIONS

Communication for EU App. No. 18275025.7, filed Feb. 19, 2018, communication dated Aug. 6, 2018.
(Continued)

*Primary Examiner* — Kelly J Bekker
*Assistant Examiner* — Mohammed S Adam
(74) *Attorney, Agent, or Firm* — Crowell & Moring LLP

(57) ABSTRACT

In one aspect of the invention, a preloaded stent graft delivery device includes a guidewire catheter having a proximal end, a distal end, and a guide wire lumen therethrough; a nose cone dilator at the proximal end of the guide wire catheter, the nose cone dilator comprising a distal end and a capsule on the distal end of the nose cone dilator; a handle assembly at the distal end of the guidewire catheter, the handle assembly comprising a first section and a second section releasably connected to the handle assembly and in communication with the capsule on the distal end of the nose cone dilator; a ratchet assembly disposed within an interior surface of the first section of the handle assembly; a pusher catheter extending from the handle assembly towards the nose cone dilator; and a sheath disposed coaxially over the pusher catheter.

13 Claims, 15 Drawing Sheets

(51) Int. Cl.
  *A61B 17/02* (2006.01)
  *A61F 2/954* (2013.01)
  *A61M 29/00* (2006.01)
  *A61F 2/06* (2013.01)
  *A61F 2/95* (2013.01)

(52) U.S. Cl.
  CPC ............ *A61F 2/954* (2013.01); *A61F 2/9517* (2020.05); *A61F 2002/061* (2013.01); *A61F 2002/9665* (2013.01); *A61M 29/00* (2013.01)

(58) Field of Classification Search
  CPC ...... A61F 2002/9522; A61F 2002/9528; A61F 2002/9534; A61M 29/00; A61B 17/0218
  See application file for complete search history.

(56) References Cited

U.S. PATENT DOCUMENTS

| | | | |
|---|---|---|---|
| 6,056,775 A | 5/2000 | Borghi et al. | |
| 6,524,335 B1 | 2/2003 | Hartley et al. | |
| 6,652,567 B1 | 11/2003 | Deaton | |
| 6,663,665 B2 | 12/2003 | Shaolian et al. | |
| 6,761,733 B2 | 7/2004 | Chobotov et al. | |
| 7,326,236 B2* | 2/2008 | Andreas | A61F 2/95 623/1.11 |
| 7,435,253 B1 | 10/2008 | Hartley et al. | |
| 7,537,606 B2 | 5/2009 | Hartley et al. | |
| 7,550,001 B2* | 6/2009 | Dorn | A61F 2/95 623/1.12 |
| 7,591,846 B2 | 9/2009 | Vardi | |
| 7,651,519 B2 | 1/2010 | Dittman | |
| 7,780,717 B2* | 8/2010 | Ducke | A61F 2/95 623/1.11 |
| 8,012,193 B2 | 9/2011 | Hartley et al. | |
| 8,118,854 B2 | 2/2012 | Bowe | |
| 8,128,686 B2 | 3/2012 | Paul, Jr. et al. | |
| 8,333,797 B2 | 12/2012 | Goodson, IV et al. | |
| 8,523,931 B2 | 9/2013 | Mayberry et al. | |
| 8,540,759 B2 | 9/2013 | Porter | |
| 8,556,961 B2 | 10/2013 | Quinn | |
| 8,663,306 B2 | 3/2014 | Kasprzak et al. | |
| 8,709,061 B2 | 4/2014 | Greenberg et al. | |
| 8,747,455 B2 | 6/2014 | Greenberg | |
| 8,753,385 B2 | 6/2014 | Hartley et al. | |
| 8,845,708 B2 | 9/2014 | Hartley et al. | |
| 9,226,814 B2* | 1/2016 | Jensen | A61F 2/07 |
| 9,622,894 B2* | 4/2017 | McGee | A61F 2/82 |
| 2004/0215229 A1 | 10/2004 | Coyle | |
| 2004/0260383 A1* | 12/2004 | Stelter | A61F 2/07 623/1.11 |
| 2005/0033403 A1* | 2/2005 | Ward | A61F 2/95 623/1.11 |
| 2005/0149159 A1* | 7/2005 | Andreas | A61F 2/95 623/1.11 |
| 2007/0088424 A1* | 4/2007 | Greenberg | A61F 2/954 623/1.12 |
| 2007/0168013 A1 | 7/2007 | Douglas | |
| 2007/0168014 A1* | 7/2007 | Jimenez | A61F 2/95 623/1.12 |
| 2007/0299499 A1* | 12/2007 | Hartley | A61F 2/962 623/1.11 |
| 2008/0255653 A1 | 10/2008 | Schkolnik | |
| 2010/0036472 A1* | 2/2010 | Papp | A61F 2/95 623/1.11 |
| 2010/0094400 A1* | 4/2010 | Bolduc | A61B 17/00234 623/1.11 |
| 2010/0168756 A1* | 7/2010 | Dorn | A61F 2/95 606/108 |
| 2010/0174290 A1* | 7/2010 | Wuebbeling | A61F 2/95 606/108 |
| 2011/0034987 A1* | 2/2011 | Kennedy | A61F 2/95 623/1.11 |
| 2011/0054594 A1* | 3/2011 | Mayberry | A61F 2/07 623/1.34 |
| 2011/0288558 A1* | 11/2011 | Nimgaard | A61F 2/95 606/108 |
| 2011/0307048 A1* | 12/2011 | Ivancev | A61F 2/07 623/1.11 |
| 2012/0041535 A1 | 2/2012 | Huser et al. | |
| 2012/0041537 A1* | 2/2012 | Parker | A61F 2/95 623/1.11 |
| 2012/0059448 A1* | 3/2012 | Parker | A61F 2/95 623/1.11 |
| 2012/0109279 A1 | 5/2012 | Mayberry et al. | |
| 2012/0239130 A1 | 9/2012 | Hartley et al. | |
| 2013/0131775 A1 | 5/2013 | Hadley et al. | |
| 2013/0274859 A1 | 10/2013 | Argentine | |
| 2013/0289692 A1* | 10/2013 | Argentine | A61F 2/966 623/1.11 |
| 2014/0025149 A1 | 1/2014 | Devereux | |
| 2014/0058402 A1 | 2/2014 | Havel | |
| 2014/0180394 A1 | 6/2014 | Greenberg et al. | |
| 2014/0257454 A1* | 9/2014 | McGee | A61F 2/966 623/1.11 |
| 2014/0277330 A1 | 9/2014 | Roeder | |
| 2014/0350658 A1 | 11/2014 | Benary et al. | |
| 2015/0094794 A1* | 4/2015 | Cummins | A61F 2/966 623/1.11 |
| 2015/0250631 A1* | 9/2015 | Cummins | A61F 2/966 606/108 |
| 2016/0022456 A1* | 1/2016 | Butler | A61F 2/962 623/1.12 |
| 2016/0175132 A1* | 6/2016 | Wilger | A61F 2/97 623/1.11 |
| 2016/0220369 A1* | 8/2016 | Chalekian | A61F 2/2436 |
| 2016/0302950 A1* | 10/2016 | Marmur | A61F 2/07 |

FOREIGN PATENT DOCUMENTS

| | | |
|---|---|---|
| EP | 3 095 420 | 11/2016 |
| EP | 3 369 402 A1 | 9/2018 |
| WO | 2012164295 | 12/2012 |
| WO | 2015075708 | 5/2015 |

OTHER PUBLICATIONS

Extended European Search Report for EP Application No. 18275025.7 dated Jan. 27, 2022 (4 pages).

\* cited by examiner

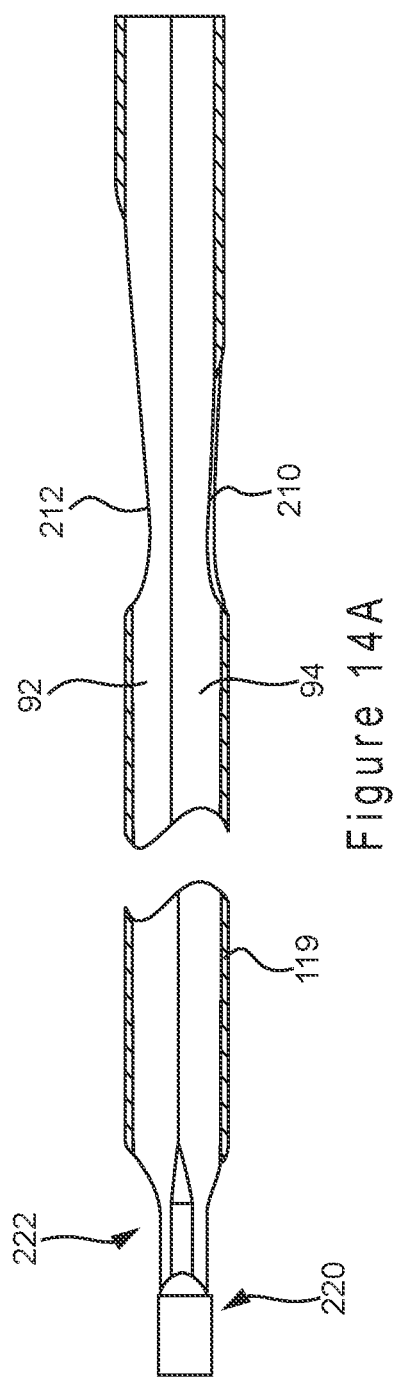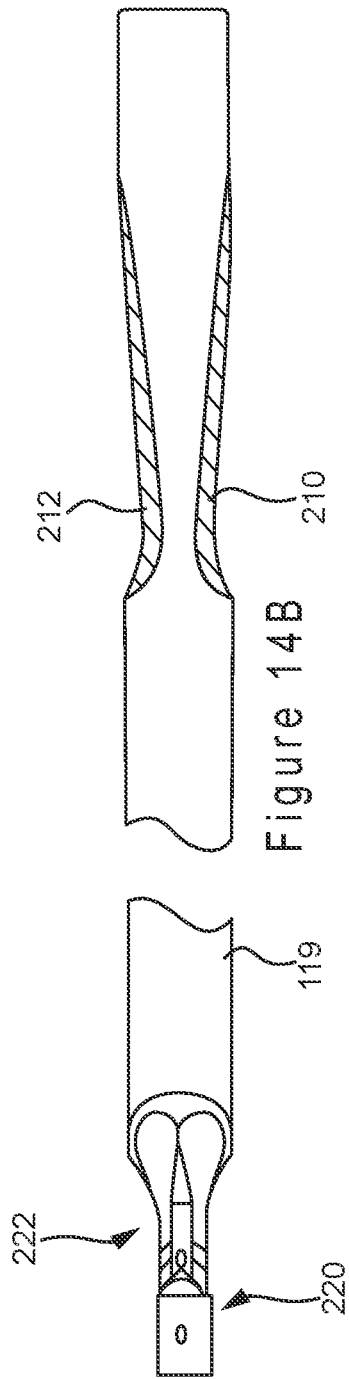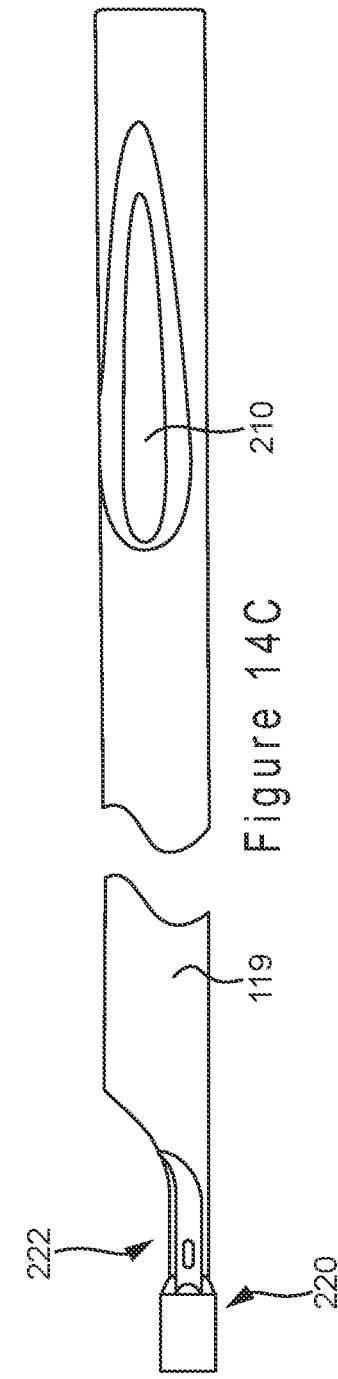

DELIVERY SYSTEM FOR A PRELOADED FENESTRATED DEVICE HAVING A RATCHETED WIRE RELEASE

RELATED APPLICATION

This application claims the benefit of U.S. Provisional Patent Application Ser. No. 62/464,473 filed Feb. 28, 2017, which is incorporated by reference in its entirety.

BACKGROUND

1. Technical Field

This invention relates to a medical device and more particularly to a device for introduction or delivery of a stent graft into the vasculature of a patient.

2. Background Information

It is known to introduce endovascular stent grafts into the vasculature of a patient to bridge an aneurism or damaged portion of the wall of the vasculature. In the deployment of a graft or stent graft into the human or animal body via intraluminal techniques a deployment device is used to introduce the graft into a lumen of the body and, after the graft has been deployed and expanded within the lumen, the introducer needs to be retracted.

Today, many endoluminal prostheses are radially self-expanding. Radially self-expanding prostheses are advantageous because they do not require complicated and bulky balloon catheter systems for deployment. Such prostheses present a challenge, however, in that once a prosthesis end is released and anchored into the body lumen, subsequent positioning can be difficult. This is particularly the case if the ends of the prosthesis include anchoring mechanisms to secure the prosthesis to the body lumen. As a consequence, many deployment devices have been proposed that allow the self-expanding prosthesis to be partially expanded while providing a mechanism for retaining the prosthesis ends until the prosthesis has been properly positioned.

Problems can occur, however, where the damage to the vasculature includes or is adjacent to a branch vessel from a main artery because the branch vessel may be occluded by the stent graft and cause permanent damage to the patient. Examples of such branch vessels are the renal and the mesenteric arteries extending from the aorta.

Fenestrations in a stent graft have been proposed to allow access to a branch vessel from a main stent graft but it is often necessary to provide a side branch graft to maintain access into the branch vessel. Catheterisation of such a branch vessel from a delivery device through the fenestration enables deployment of a covered stent or uncovered stent into the branch vessel. This invention provides an improved apparatus for catheterisation and deployment of side branch grafts.

BRIEF SUMMARY

In one aspect of the invention, a preloaded stent graft delivery device includes a guidewire catheter having a proximal end, a distal end, and a guide wire lumen therethrough; a nose cone dilator at the proximal end of the guide wire catheter, the nose cone dilator comprising a distal end and a capsule on the distal end of the nose cone dilator; a handle assembly at the distal end of the guidewire catheter, the handle assembly comprising a first section and a second section releasably connected to the handle assembly and in communication with the capsule on the distal end of the nose cone dilator; a ratchet assembly disposed within an interior surface of the first section of the handle assembly; a pusher catheter extending from the handle assembly towards the nose cone dilator, the pusher catheter comprising at least one lumen therethrough where the guidewire catheter extends through the at least one lumen within the pusher catheter; a sheath disposed coaxially over the pusher catheter, wherein the sheath has two longitudinal slits along a portion of the length of the sheath. In some embodiments, the pusher catheter further comprises two longitudinal auxiliary lumens. In alternative embodiments, the first section of the trigger wire release assembly is rotatable about a longitudinal axis.

In another aspect of the invention, a preloaded stent graft delivery device includes a guidewire catheter having a proximal end, a distal end, and a guide wire lumen therethrough; a trigger wire release assembly at the distal end of the guidewire catheter, the trigger wire release assembly comprising a rotatable section, a ratchet assembly within an interior surface of the rotatable section of the trigger wire release assembly; a spool within an interior surface of the rotatable section, the spool positioned proximal to the ratchet assembly; and, a sheath at least partially disposed coaxially over the guidewire catheter. In some embodiments, the rotatable section of the trigger wire release assembly is rotatable about a longitudinal axis. In alternative embodiments, the ratchet assembly comprises a ratchet surface and a pawl engaged with the ratchet surface.

In yet another aspect of the invention, a preloaded stent graft delivery device, includes a guidewire catheter having a proximal end, a distal end, and a guide wire lumen therethrough; a nose cone dilator at the proximal end of the guide wire catheter, the nose cone dilator comprising a distal end and a capsule on the distal end of the nose cone dilator; a handle assembly at the distal end of the guidewire catheter, the handle comprising a rotatable section and a releasable section distal to the rotatable section, the releasable section in communication with the capsule on the distal end of the nose cone dilator; a ratchet assembly disposed within an interior surface of the rotatable section of the handle assembly, the ratchet assembly comprising a ratchet surface and a pawl engaged with the ratchet surface; a spool within the interior surface of the rotatable section, the spool positioned proximal to the ratchet assembly; a trigger wire having a distal end and a proximal end, the proximal end being arranged to selectively couple the trigger wire release assembly to a prosthesis, the distal end coupled to the spool within the interior surface of the rotatable section; a pusher catheter extending from the handle assembly towards the nose cone dilator, the pusher catheter comprising at least one lumen therethrough where the guidewire catheter extends through the at least one lumen within the pusher catheter; and, a sheath disposed coaxially over the pusher catheter.

BRIEF DESCRIPTION OF THE DRAWINGS

FIGS. 14A to 14D show various views of the pusher catheter of the embodiment of the stent graft delivery device shown in FIG. 1.

DETAILED DESCRIPTION OF THE DRAWINGS AND THE PRESENTLY PREFERRED EMBODIMENTS

Figure 1:
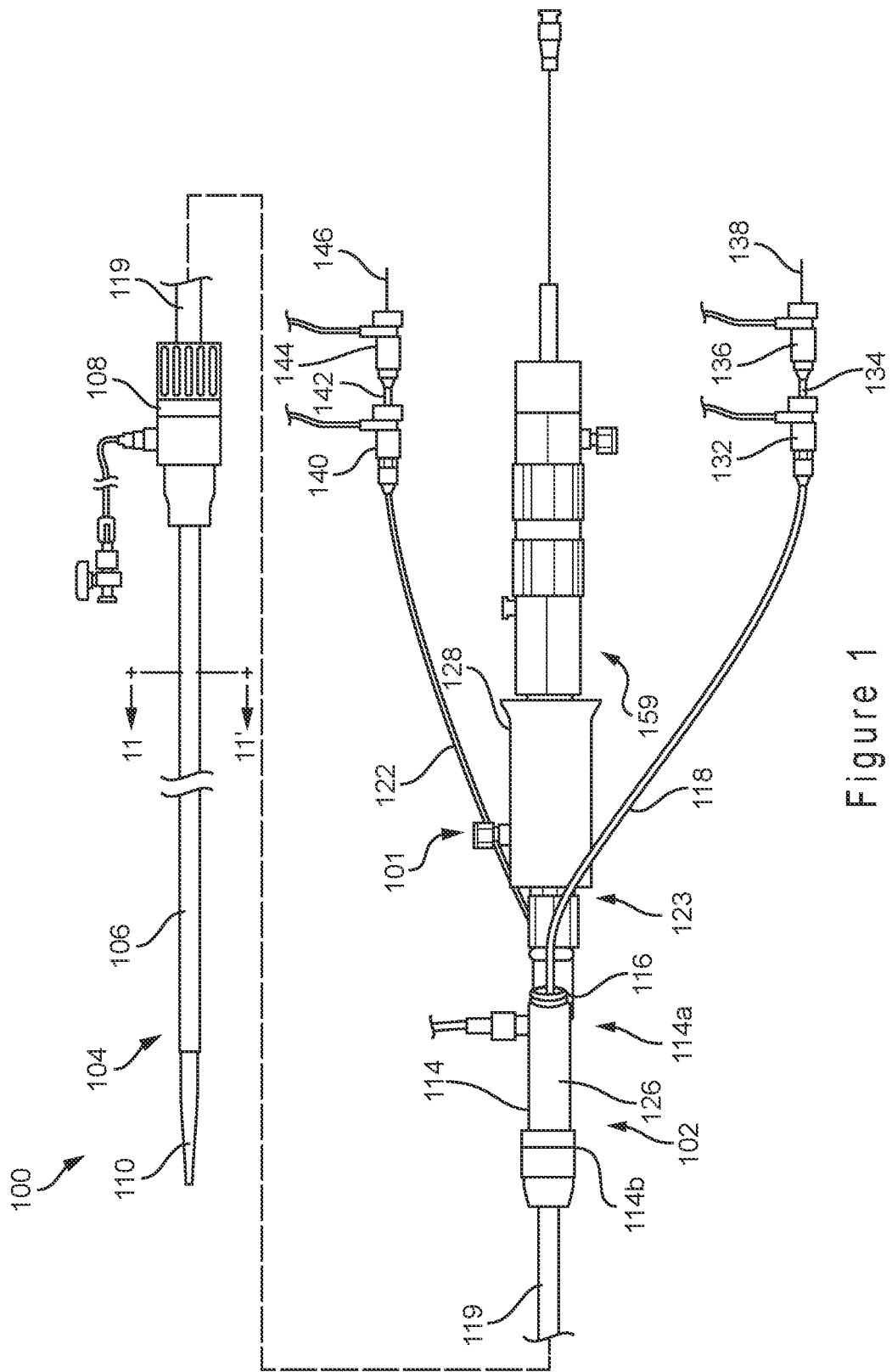
FIG. 1 shows an embodiment of a pre-loaded stent graft delivery device according to the present invention.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

The term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the prosthesis delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first, and the outflow end (that end from which the fluid exits). When applied to other vessels similar terms such as caudal and cranial should be understood.

The term "fenestration" means an opening provided through a surface of a prosthesis from the interior of the prosthesis to the exterior of the prostheses and may have a variety of geometries, including circular, semi-circular, oval, oblong, as well as other geometries.

The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPONT. Dacron™ is known to be sufficiently biologically inert, non-biodegradable, and durable to permit safe insertion inside the human body.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated. The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The term "stent" means any device or structure that adds rigidity, expansion force or support to a prosthesis. A stent is used to obtain and maintain the patency of the body passageway while maintaining the integrity of the passageway. Also, the stent may be used to form a seal. The stent may be located on the exterior of the device, the interior of the device, or both. A stent may be self-expanding, balloon-expandable or may have characteristics of both. A variety of other stent configurations are also contemplated by the use of the term "stent." The stents 16 may be comprised of a metallic material selected from stainless steel, silver, platinum, palladium, gold, titanium, tantalum, iridium, tungsten, cobalt, chromium, cobalt-chromium alloy 1058, cobalt-based 35 N alloy, nickel-based alloy 625, a molybdenum alloy, a molybdenum alloy including about 0.4% to about 0.8% of lanthanum oxide (Li2O3), and a nickel-titanium alloy, such as nitinol, or other suitable materials as known in the art. The stents may be made of a wire, or may be laser or cannula cut, or manufactured by other known methods.

The terms "patient," "subject," and "recipient" as used in this application refer to any animal, especially humans.

As shown in FIG. 1, the delivery device 100 comprises a handle 101 and manifold assembly 102 and introduction portion 104 intended to be deployed into the patient by the known Seldinger method. More specifically the introduction portion 104 includes a sheath 106 extending from a sheath hub 108 to a nose cone dilator 110. A stent graft 131 is retained within the outer sheath 106 in the region 107 just distal of the nose cone dilator 110. A sheath hub 108 is positioned over a tri-lumen catheter 119 which extends from and is connected into a manifold 114 as is discussed in more detail below. The manifold 114 has a proximal end 114*b* into which is affixed the tri-lumen catheter 119 and two access ports 116, 120 at its distal end 114*a*.

A handle 101 comprising a handle assembly 123 for the stent graft delivery device 100 is provided. In one embodiment, a trigger wire release mechanism 159 is adjacent to the handle assembly 123. The handle assembly 123 comprises a front handle 126 and a back handle 128. The manifold 114 forms part of the front handle 126. It is understood that the manifold 114 can be separate from the front handle 126 and can be disposed either proximal or distal to the front handle 126. The manifold 114 includes an access port 116 for a first access sheath 118 that extends from the manifold portion 114 of the front handle 126. Access port 120 is provided for a second access sheath 122. The access ports 116, 118 include haemostatic seals 117, 121. The first access sheath 118 extends to a haemostatic seal 132 through which extends a dilator 134. On the dilator 134 is a dilator haemostatic seal 136 through which extends an indwelling guide wire 138. Likewise, the second access sheath 122 extends to a haemostatic seal 140 through which extends a dilator 142. On the dilator 142 is a dilator haemostatic seal 144 through which extends an indwelling guide wire 146. Further, the access sheaths 118, 122 (left and right) on their respective indwelling guide wires 138, 146 will already be disposed within the lumen of stent graft 131 such that the step of advancing the access sheaths 118, 122 and guide wires 138, 146 within the lumen of the stent graft 131 after the placement of the device 100 within the patient is not required.

Figure 2:
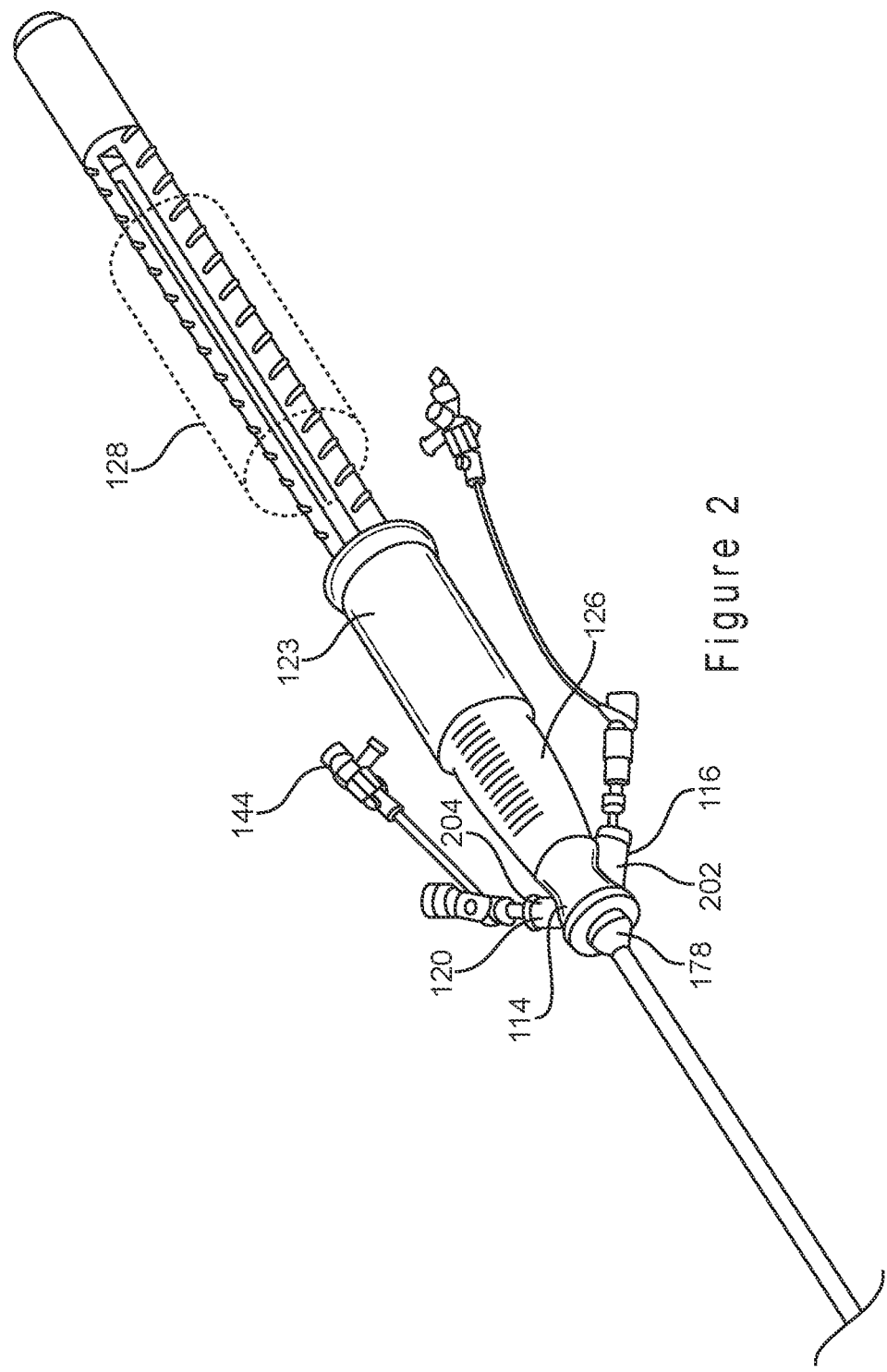
FIG. 2 is a prospective view of the distal portion of the embodiment of the stent graft delivery device of FIG. 1.

FIG. 2 illustrates an embodiment of the handle assembly 123. The handle assembly 123 includes a front handle 126 and a back handle 128 disposed distal to the front handle 126. The manifold 114 forms part of the front handle 126. The manifold 114 includes an access port 116 for a first access sheath 118 that extends from the manifold portion 114 of the front handle 126. Access port 120 is provided for a second access sheath 122. The access ports 116, 118 include haemostatic seals 117, 121. The manifold 114 forms part of the front handle 126. It is understood that the manifold 114 can be separate from the front handle 126 and can be disposed either proximal or distal to the front handle 126. The back handle 128 is disposed distal to the front handle 126. The back handle portion 128 is disposed about a sheath mount 148.

Figure 3:
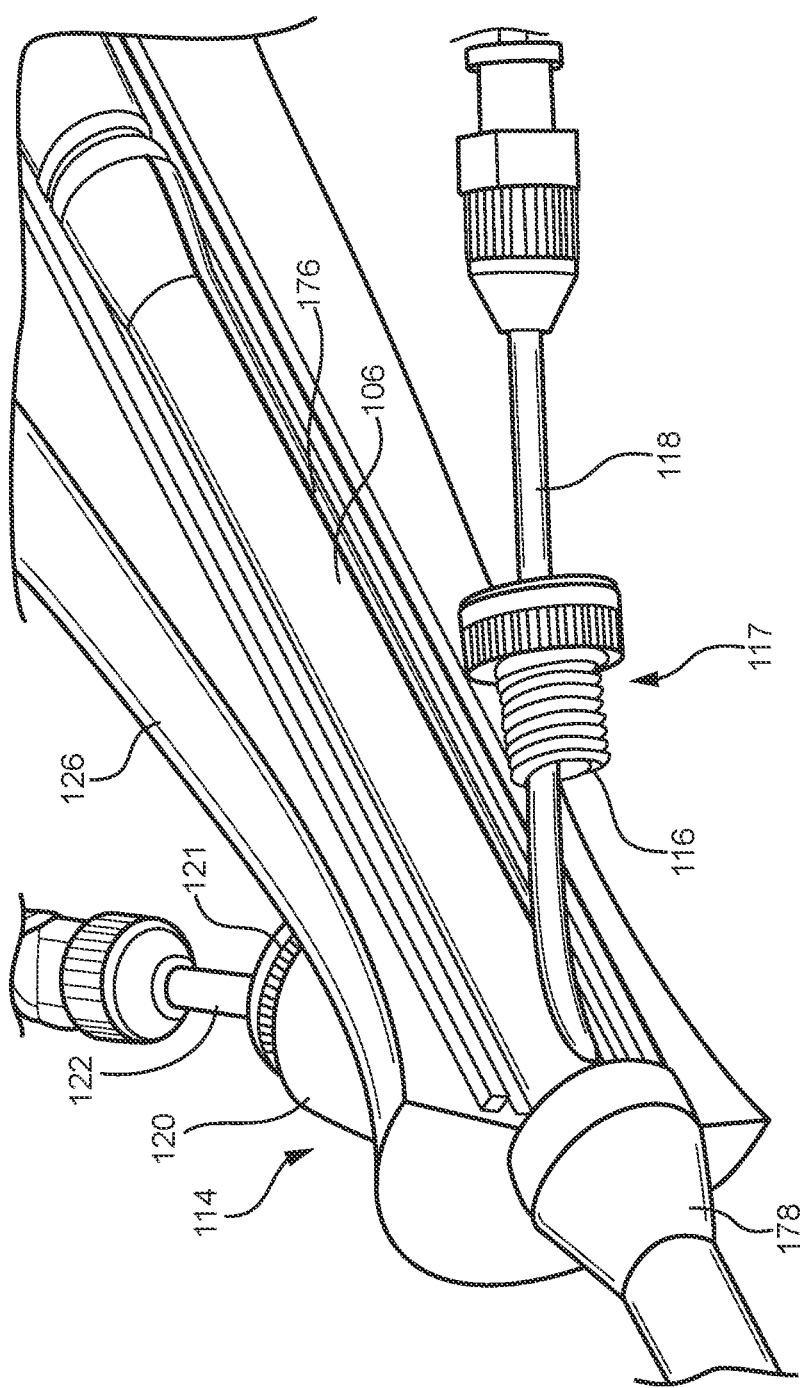
FIG. 3 shows a partial cross-sectional view of a handle portion of the embodiment of the stent graft delivery device of FIG. 1.
Figure 9:
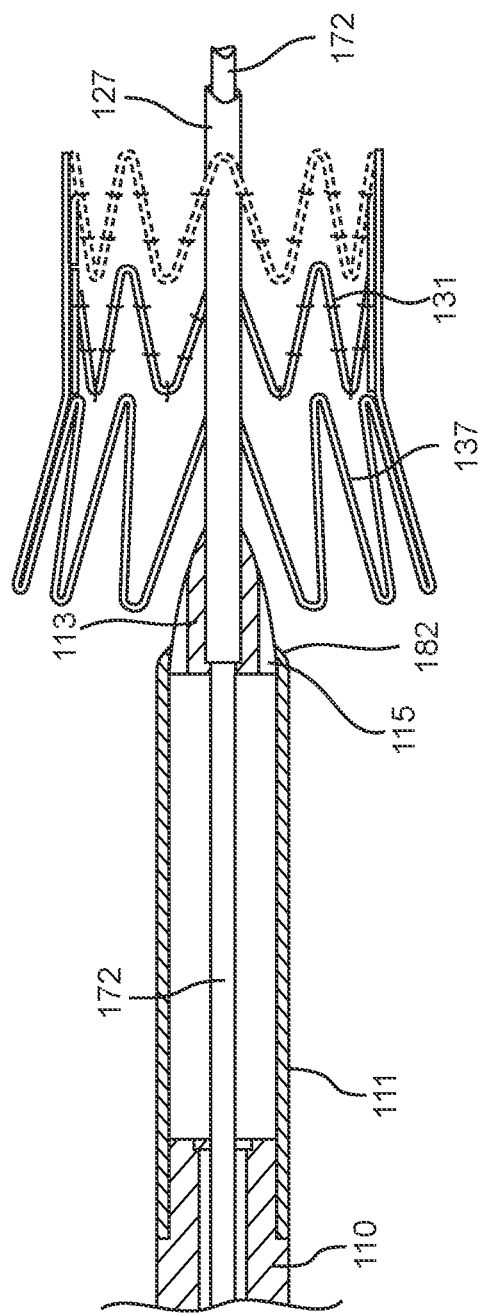
FIG. 9 shows a cross-sectional view of part of a nose cone dilator and capsule of the stent graft delivery device of FIG. 1.

FIG. 3 illustrates a transverse cross-section of the front handle. A portion of the sheath 106 includes a split 176 on either side so as to allow access into the interior of the sheath 106. The splits 176 allow for the preloading of the access sheaths 118, 122. The gap of the split 176 is sufficiently large enough to allow for the sheath 106 to be retracted while the access sheaths 118, 122 are preloaded within the manifold 114. Thus, the maximum opening of each split 176 may be equal to the outer diameter of the access sheaths 118, 122, which in one embodiment is 6 fr. The length of each split 176 varies and can be as small as 1 mm or as long as 40 mm or greater. The length of the splits 176 may extend from a proximal end of the sheath 106 and may terminate at a location of the sheath 106 that is distal to the handle assembly 123. The splits 176 also allow the sheath 106 to be retracted, by rotation of the back handle 128, while the access sheaths 118, 122 remain in the tri lumen catheter 119. As shown in FIGS. 2 and 9, the splits 176 allow for continuous access to the tri-lumen catheter 119 via the apertures 210, 212 during deployment process of the main stent graft 131. This allows the main stent graft 131 to be deployed while the access sheaths 118, 122, which contain the pre-loaded stent grafts for the side branches, remain in the tri-lumen catheter 119. Upon deployment of the main stent graft 131, the side branch stent grafts may be inserted in the side branches in the matter described below so as to cannulated the side branches. The step of inserting the access sheaths 118, 122 into the manifold 114 after the deployment of the main stent graft 131 and the related steps are eliminated. A secondary sheath 178 is disposed about the sheath 106. The length of the secondary sheath 178 is approximately equal to the length of the splits 176 in the sheath 106. The function of the thin secondary sheath is to direct blood flow from the splits 176 in the sheath 106 back into the patient's body.

Figure 4:
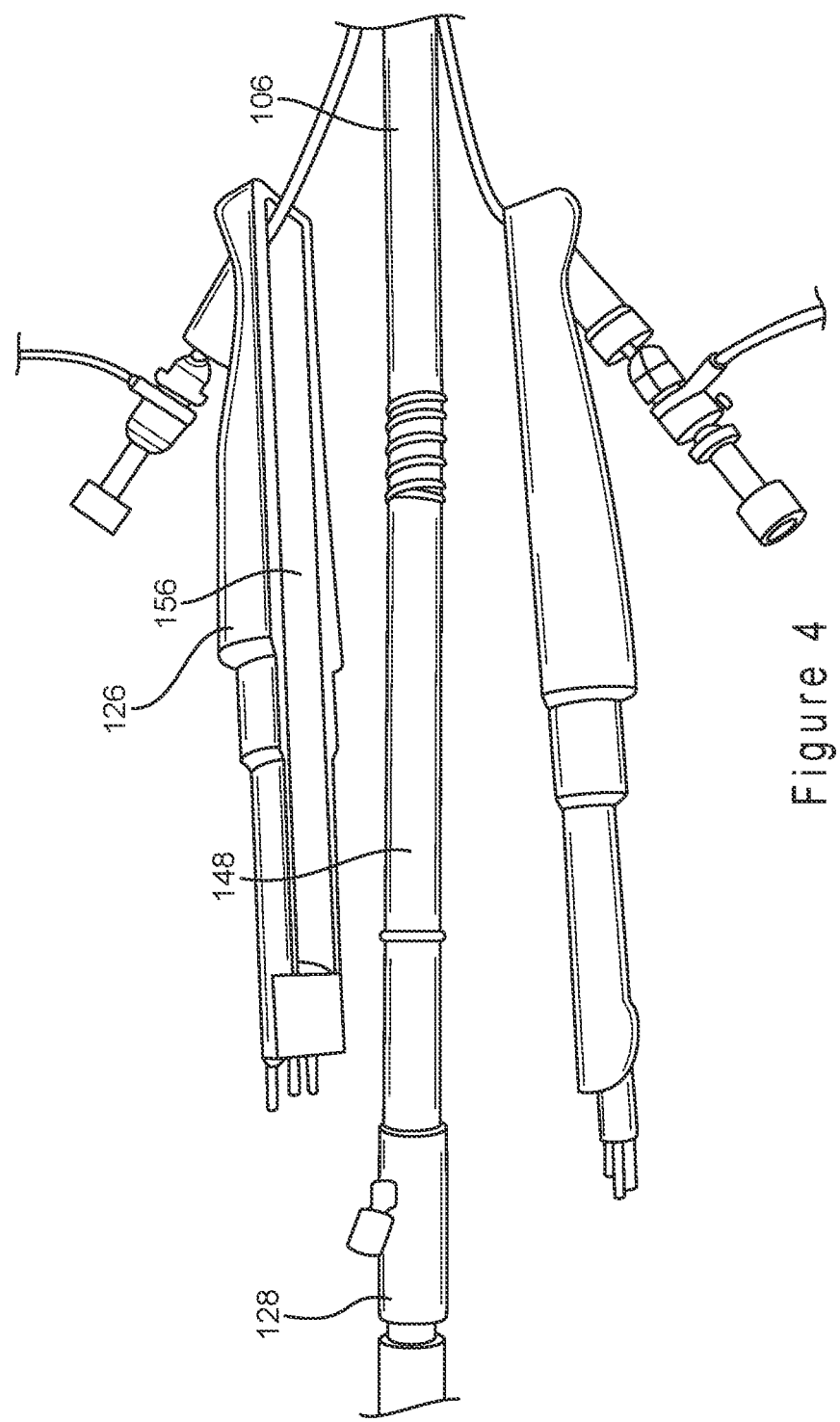
FIG. 4 is a partial cross-sectional view of a distal portion of the handle portion of the embodiment of the stent graft delivery device of FIG. 1.
Figure 5:
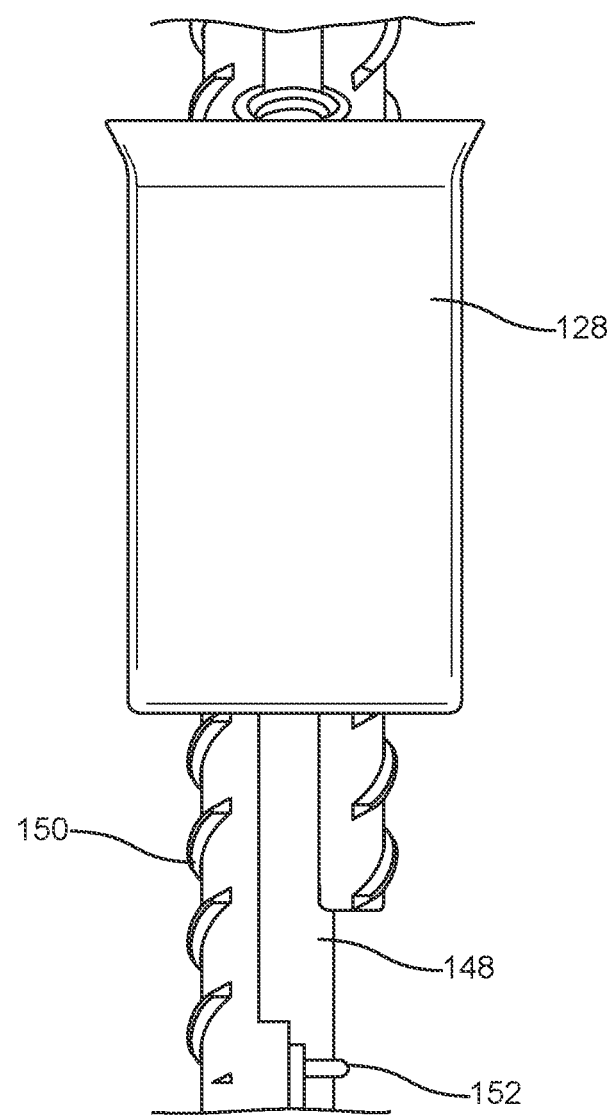
FIG. 5 shows the distal portion of the embodiment of the stent graft delivery device of FIG. 1 and in particular detail the handle portion.

As shown in FIGS. 4 and 5, the sheath mount 148 is received within an inner groove 156 formed within the front handle 126. The series of threads 150 is disposed along a portion of the length of the sheath mount 148. The back handle portion 128 is slidingly received over the series of threads 150 such that the back handle portion can rotate about the sheath mount 148 along the threads 150. The back handle portion 128 travels along a longitudinal axis defined by the length of the sheath mount 148 as it is rotated. The sheath mount 148 includes front and back O-rings 152, 154, as shown in FIG. 5, to seal any space between the sheath mount 148 and threads 150.

The sheath mount 148 extends through the handle assembly 123 as shown in FIG. 5. The sheath mount 148 is in communication with three parts in the device 100. The first is the sheath 106, which is fixed to the sheath mount 148 by a pin vice or an adhesive. The sheath mount 148 is also in communication with the tri lumen pusher (not shown). The sheath mount 148 slides over the top of the tri-lumen pusher (not shown) and is kept concentric to the rest of the device 100. The sheath mount 148 is also coupled with the back handle 128. A portion of the back handle 128 mates with the sheath mount 148 and pushes it linearly as the back handle 128 is twisted along a series of threads 150. Specifically, the sheath mount 148 further includes an abutment portion (not shown) that engages the back handle 128 such that the sheath mount 148, and sheath 106, translate along the longitudinal axis of the sheath mount 148 as the back handle 128 is rotated.

Referring back to FIG. 1, trigger wire release assembly 159 includes a rotational portion 160 and a releasable portion 162. As shown, the rotational portion 160 includes a proximal thumbhandle 164 and a distal thumbhandle 166. The rotational portion is configured to be rotated about a longitudinal axis of the delivery device 10 by a user of the device 10. In this embodiment, the rotational portion may be coupled with the trigger wires associated with the stabilization retention of indwelling guide wires, a retention trigger wire for an exposed stent 137 of the stent graft 131 in the capsule 143, and the diameter reducing ties for the stent graft 131. The releasable portion of the trigger wire release assembly 159 is positioned distal to the rotational portion of the trigger wire release assembly. The releasable portion 162 of the trigger wire assembly 159 is held in place upon the trigger wire release assembly by a set screw 174. In this embodiment, the trigger wire for the distal end of the stent graft 131 is coupled to the releasable portion of the trigger wire. It is appreciated that the number of trigger wires coupled to either the rotatable portion of the trigger wire arrangement or the releasable portion of the trigger wire assembly will vary depending on the number of stents to be deployed within the vessels. A pin vice arrangement 170 is positioned at a distal end of the releasable portion of the trigger wire release assembly. The pin vice arrangement 170 locks movement of a guide wire catheter 172 with respect to the distal portion of the handle 128 and the trigger wire release assembly 159 and can be loosened to allow relative motion between these components.

Figure 6:
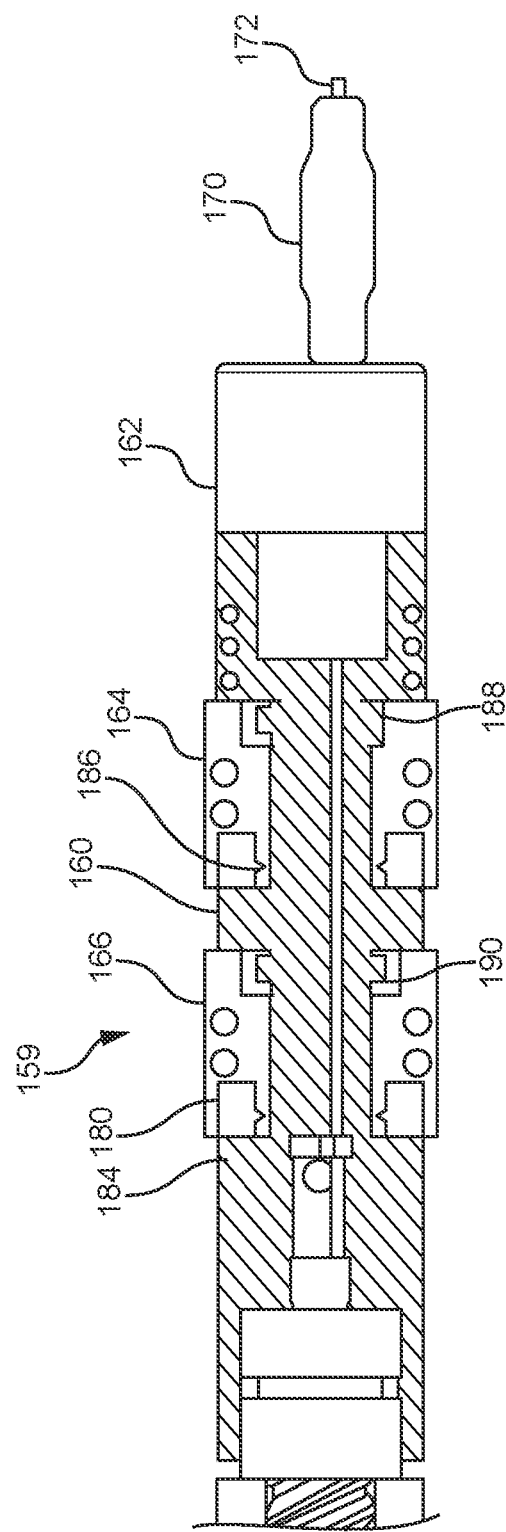
FIG. 6 shows a cross-sectional view of the trigger wire assembly of the embodiment of the stent graft delivery device of FIG. 1.

FIG. 6 illustrates a cross section of a trigger wire arrangement of the stent delivery system. The trigger wires are removed so that the aspects of the interior of the trigger wire release assembly may be seen clearly. The trigger wire release assembly 159 includes a rotational portion 160 and a releasable portion 162. The rotational portion 160 includes a proximal thumbhandle 164 and a distal thumbhandle 166. Positioned within both the proximal thumbhandle 164 and the distal thumbhandle 166, a spool 180, 183 is provided. Each spool 180, 183 includes a v-shaped groove 184, 186. The v-shaped groove allows for the trigger wire to be wound about the spool upon rotation of rotational portion 160. A ratchet assembly 188, 190 is provided within an interior surface of both the proximal thumbhandle 164 and the distal thumbhandle 166. The ratchet assembly is configured to allow the proximal thumbhandle and the distal thumbhandle to rotate in a single direction in order to prevent backwards motion of the trigger wires during release. This feature also allows for increased control of the release of the trigger wires by the user of the stent graft delivery device 10.

When the rotational portion of the trigger wire assembly is rotated, the wires wrap into the spool and utilize the circumference of the spool 180 to achieve proper wire travel upon release. Advantageously, due to the winding of the trigger wires upon the spool, the trigger wires remain completely within the interior of the trigger wire assembly. A mechanical advantage, or force amplification, is achieved through the use of this type of release mechanism for the trigger wires as compared to other release mechanisms. In particular, the mechanical advantage is based on a wheel and axle model and is calculated as a ratio of the radius of the wheel to the radius of the axle. The mechanical advantage for this aspect of the present invention is calculated as follows:

$$\frac{d_t}{d_s} = MA$$

where $d_t$ is the outer diameter of the thumbhandle and $d_s$ is the outer diameter of the spool. This mechanical advantage reduces the amount of force required to remove the trigger wires. It will be appreciated that this ratio may be modified based on the application.

Figure 7:
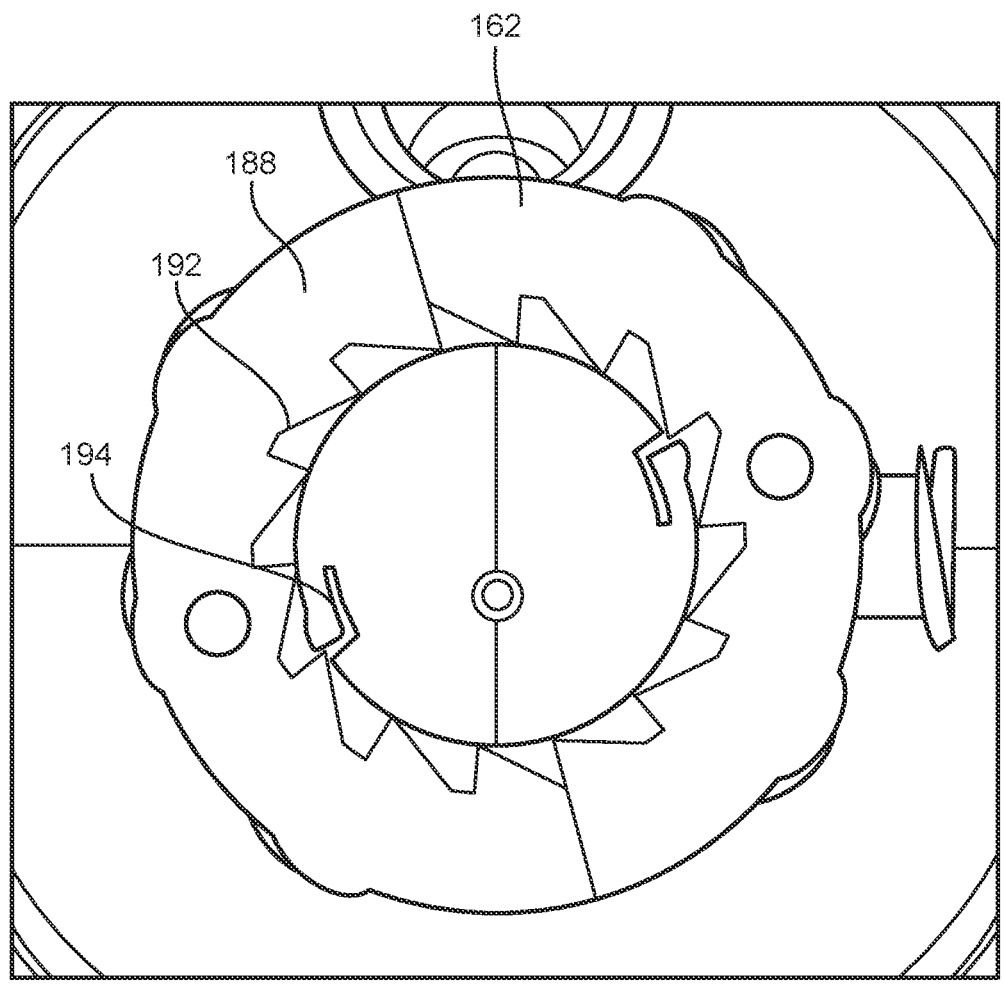
FIG. 7 shows a cross-sectional view of an assembly of a manifold and pusher chatter of the embodiment of the stent graft delivery device of FIG. 1.

FIG. 7 illustrates a cross-section of the ratchet assembly 188 of the rotational portion 162 of the trigger wire release assembly 159. As shown, the ratchet assembly 188 includes a ratchet surface 192 and a ratchet pawl 194. The ratchet surface is positioned in a distal end of the proximal thumbhandle 162 and the distal thumbhandle 164. The ratchet surface includes a plurality of teeth 193 having an asymmetric configuration. Each tooth has a moderate slope on one edge and a must steeper slope on an opposite edge. When the proximal thumbhandle 162 and/or the distal thumbhandle 164 is rotated in one direction (in this embodiment, in a counter-clockwise direction), the pawl will slide within the teeth without restricting the natural motion of the proximal thumbhandle 162 or the distal thumbhandle 164. When the direction is reversed, the pawl is configured to engage with the steep slope on the ratchet surface and will impede motion in that direction. Accordingly, the ratchet assembly 188 holds the proximal thumbhandle 162 and/or the distal thumbhandle against rotation in a clockwise direction. In use, the ratchet assembly 188 prevents any forward motion (i.e. movement in a proximal direction) of the trigger wires upon release from the stent graft delivery device 10.

Figure 8:
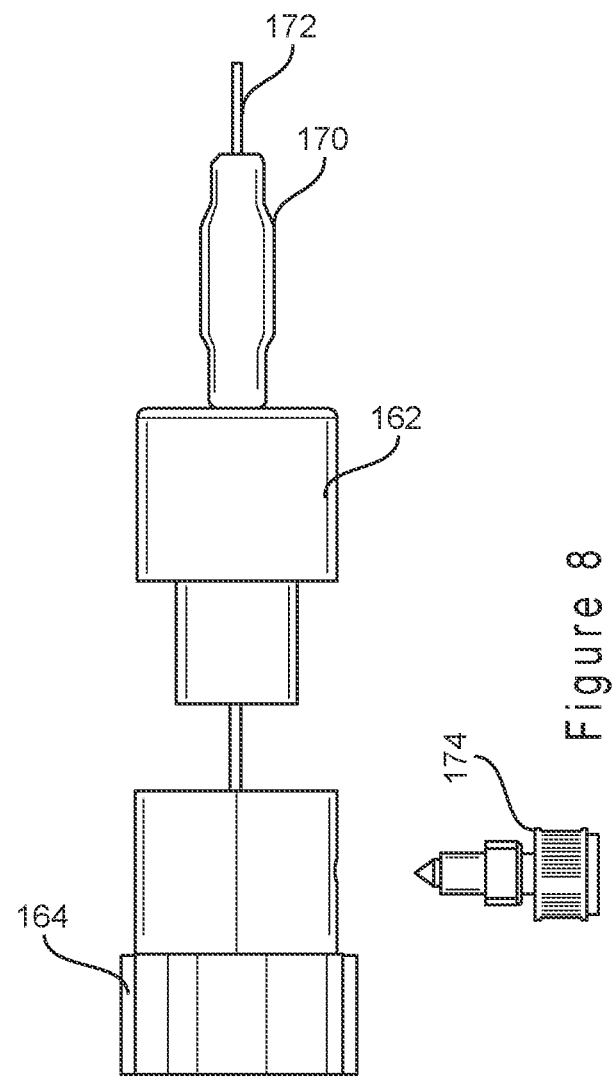
FIG. 8 shows an embodiment of the releaseable portion of an embodiment of the trigger wire assembly of the embodiment of the stent graft delivery device of FIG. 1.

FIG. 8 illustrates the releaseable portion 162 of an embodiment of the trigger wire assembly 159 in a released position. To release the releasable portion 162 of the trigger wire assembly from the trigger wire assembly 159, a user unscrews the set screw 174 from the trigger wire assembly 159. Once the set screw has been unscrewed, the releaseable portion 162 is moved in a distal direction away from the trigger wire assembly 159. As shown, the pin vice 170 and the guide wire assembly are in abutting relation to the releasable portion 162 of the trigger wire assembly 159. This distal movement of the releasable portion 162 translates to motion of the pin vice 170 and guide wire catheter 172. The distal movement of the releaseable portion 162 of the trigger assembly retracts the top capsule 111 to the tri-lumen catheter 119. In addition, as the trigger wire for the distal end of the stent graft 131 is coupled to the releasable portion, the distal movement of the releasable portion 162 of the trigger wire assembly 159 also releases the trigger wire from the distal end of the stent graft 131.

As shown FIGS. 1 and 9, the introduction portion 104 of the stent graft delivery device 100 includes the nose cone dilator 110 and at the distal end of the nose cone dilator 110 is a distally opening capsule 111 for the receipt of an exposed stent 137 of a stent graft 131. The capsule 111 has a slightly in-turned distal end 182. This has two purposes, a first is to assist with engagement of the sheath 106 of the delivery device when the nose cone dilator 110 is retracted into the sheath 106 and a second is to prevent complete withdrawal of a distal retrieval taper device 113 from the capsule as will be discussed below. The guide wire catheter 172 passes through and is fastened to the nose cone dilator 110 at its proximal end and passes through the handle assembly 123 of the delivery device 100.

The stent graft 131 shown in FIG. 9 comprises a tubular body of a biocompatible graft material such as Dacron, expanded PTFE or Thoralon, a polyurethane material. The stent graft is supported by self-expanding stents (not shown for clarity). The proximally extending exposed stent 137 assists with providing infra-renal fixation of the deployed stent graft. The stent graft 137 is retained on the delivery device 100 by proximal retention of the exposed stent 137 into the capsule 111 of the delivery device and distally by a trigger wire release mechanism 159. Diameter reducing ties can be used to hold the stent graft in a diameter reduced condition during the initial catheterisation of a side branch because it may still be necessary to move the stent graft proximally or distally or rotate it. In the diameter reduced condition this is still possible whereas when released to full diameter this may not be possible.

U.S. patent application Ser. No. 11/507,115, filed Aug. 18, 2006 entitled "Assembly of Stent Grafts" teaches the use of diameter reducing ties for stent grafts and the teachings therein are incorporated herein in their entirety. U.S. Pat. No. 7,435,253 entitled "Prosthesis and a Method of Deploying a Prosthesis" teaches arrangements for retaining a stent graft or prosthesis on a delivery or deployment device and allowing for independent rotational and translational movement of each end of the stent graft and the teachings therein are incorporated herein in their entirety.

As can be seen in FIG. 9, the distal retrieval taper device 113 fits coaxially around the guide wire catheter 172 and can move longitudinally along the guide wire catheter 172. A retrieval catheter 127 is disposed coaxially around the guide wire catheter 172 and can move longitudinally along the guide wire catheter 172. At its proximal end, the retrieval catheter 127 may joined to the distal retrieval taper device 113 and at its distal end, the retrieval catheter 127 is joined to the front handle 126 by a suitable adhesive. The distal retrieval taper device 113 used with the embodiments of the present invention may include the retrieval taper device disclosed in U.S. Pat. No. 8,876,879, filed Jun. 4, 2009 and entitled "Introducer" teaches distal retrieval taper devices (referred to therein as tapered plugs) and the teaching therein is incorporated herein in its entirety.

The distal retrieval taper device 113 has an enlarged shoulder 115 at its proximal end. The shoulder is sized so that it is of greater diameter than the smallest part of the in-turned distal end 182 of the capsule 111. By this arrangement the distal retrieval taper device 113 can move through the capsule but cannot be fully removed from the capsule, The retrieval catheter 127 is coaxial with the guide wire catheter 172. At its proximal end, the retrieval catheter 127 is affixed to the distal retrieval taper device 113 and at its distal end the retrieval catheter 127 is affixed to the front handle portion 126. This means that movement of the guide wire catheter 172 proximally with respect to the distal handle portion 129 after the release of the pin vice 170 will move the nose cone dilator 110 and capsule 111 with respect to the distal retrieval taper device 113 with the effect that the distal retrieval taper device 113 extends from the capsule thereby providing a smooth tapered surface for retrieval of the nose cone dilator through the stent graft. Locking of the pin vice after the distal retrieval taper 113 has been moved to the distal end of the capsule 111 ensures that all of the distal retrieval taper device 113, the capsule 111, the nose cone dilator 110, and the distal handle portion 129 all move together.

By this arrangement, the nose cone dilator 110 can be moved to a distal position with respect to fenestrations 147 in the stent graft 131 so that the nose cone dilator 110 and distally opening capsule 111 neither interferes with the deployment of side branch covered or uncovered stent grafts through such fenestrations 147 nor does any subsequent retraction of the nose cone dilator 110 interfere with the deployed of side branch side branch covered or uncovered stent grafts. U.S. Pat. No. 8,118,854, filed Sep. 28, 2007 entitled "Endovascular Delivery Device" teaches apparatus and methods of deployment of stent grafts and side branch stent graft into fenestration of such stent grafts and the teaching therein is incorporated herein in its entirety. The use of the stabilization retention of the indwelling guide wire is particularly discussed therein.

Figure 10:
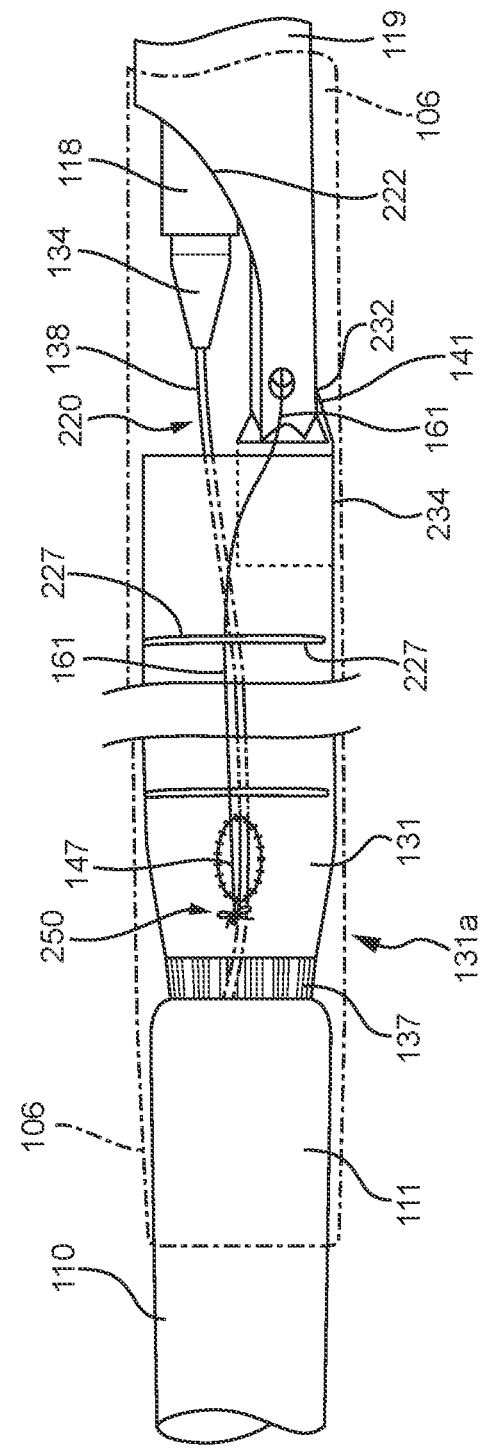
FIG. 10 shows a schematic detailed side view of a stent graft retained on the stent graft delivery device of FIG. 1.

FIG. 10 shows detail of the stent graft 131 and its retention system in the region 107 as shown in FIG. 1. In particular, there is detail shown of the distal attachment, the diameter reducing ties and the proximal retention. The stent graft 131 is retained within the sheath 106 and concentrically around the guide wire catheter 172 and retrieval catheter 127. The stent graft 131 has a fenestration 147 towards its proximal end. In use, the stent graft 131 is deployed so that the fenestration 147 is substantially aligned with a renal artery and it is intended to catheterize the renal artery through the fenestration to deploy the secondary stent graft. The secondary stent graft can be covered or uncovered side branch stent or stent graft for cannualation of the renal artery.

The stent graft 131 has a proximally extending exposed stent 137 at is proximal end 131a. In its ready to deploy condition, the proximally extending exposed stent 137 is received into the capsule 111 at the distal end of the nose cone dilator 110. At its distal end 131b the stent graft is retained to the attachment boss 220 at the proximal end of the tri-lumen catheter 119. Trigger wire 141 engages the distal end of the stent graft. Trigger wire 141 extends out of aperture 232 in the attachment boss 220 and engages into the stent graft 131 before re-entering the attachment boss through aperture 234 into the guide wire lumen 90 and exiting the guide wire lumen 90 at the proximal end of the tri-lumen catheter 119. At its distal end the trigger wire 141 is attached to the trigger wire release 166.

The stent graft 131 has diameter reducing tie arrangements to retain it in a partially diameter reduced condition even after the sheath 106 has been retracted during deployment. The diameter reducing tie arrangement are on each side of the stent graft and comprise a trigger wire 160 stitched along the graft material on either side of the stent graft and loops of filament such as suture thread 227 engaged around the trigger wire and a portion of the graft material part way around the stent graft and then drawn tight. It can be appreciated that the secondary stent grafts may also be retained within the tri lumen catheter 119 in the same manner described above with respect to the stent grant 131. U.S. patent application Ser. No. 11/507,115, filed Aug. 18, 2006 entitled "Assembly of Stent Grafts" teaches apparatus and methods of diameter reduction of stent grafts and the teaching therein is incorporated herein in its entirety.

Figure 11:
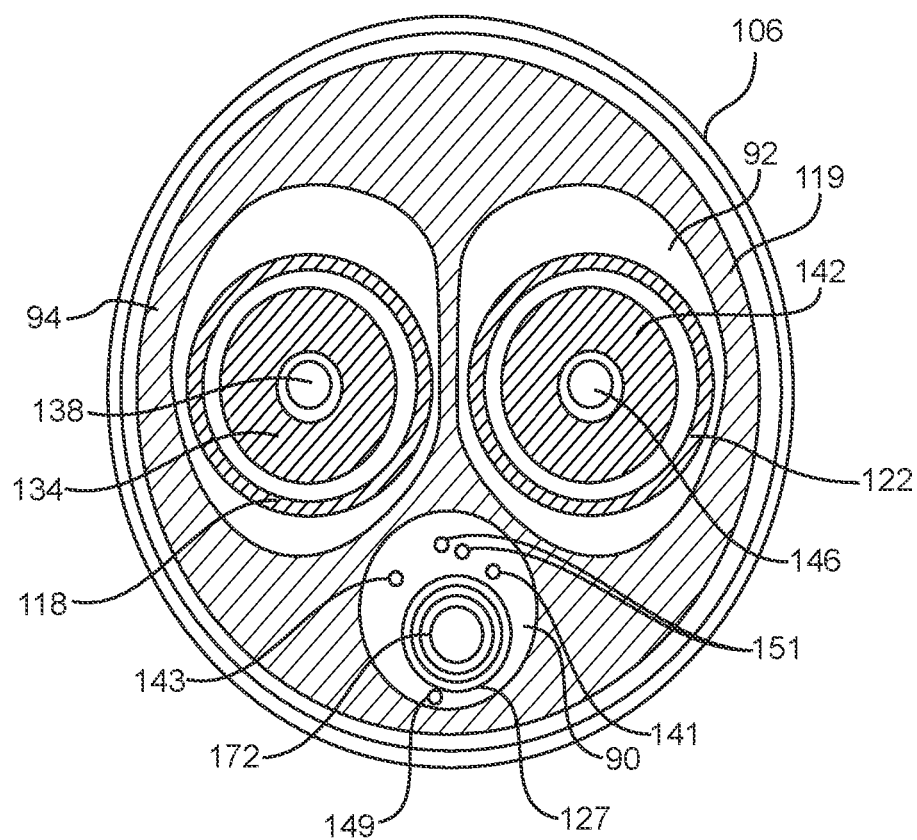
FIG. 11 shows a transverse cross-sectional view of the pusher catheter portion of the embodiment shown in FIG. 1.

As can be seen particularly in FIG. 11, which is a transverse cross section along the line 10-10' as shown in FIG. 1, the tri-lumen catheter 119 is surrounded by the sheath 106. In this embodiment, the tri-lumen catheter 119 has three longitudinally extending lumens. A first lumen is a guide wire lumen 90 and this lumen is off-set from the center of the tri-lumen catheter 119 to allow for two auxiliary lumens 92 and 94. The guide wire lumen 90 has passing through it the guide wire catheter 172 and coaxially around that the retrieval catheter 127. Extending out of the two auxiliary lumens 92 and 94 are the auxiliary catheters 122 and 118 respectively. From the proximal ends of the respective auxiliary catheters 118 and 122 extend dilators 134 and 142. The auxiliary guide wires 138 and 146 extend through the dilators and the secondary stents are also disposed therein Also in the guide wire lumen 90 are the trigger wires for the diameter reducing ties 149, the top capsule 143, the distal retention 141 and the auxiliary guide wire stabilization 151. The auxiliary lumen 94 has the first access sheath 118 extending through it and the dilator 134 and guide wire 138 extend through the first access sheath 118. The auxiliary lumen 92 has the second access sheath 122 extending through it and the dilator 142 and guide wire 146 extend through the second access sheath 122.

Figure 12:
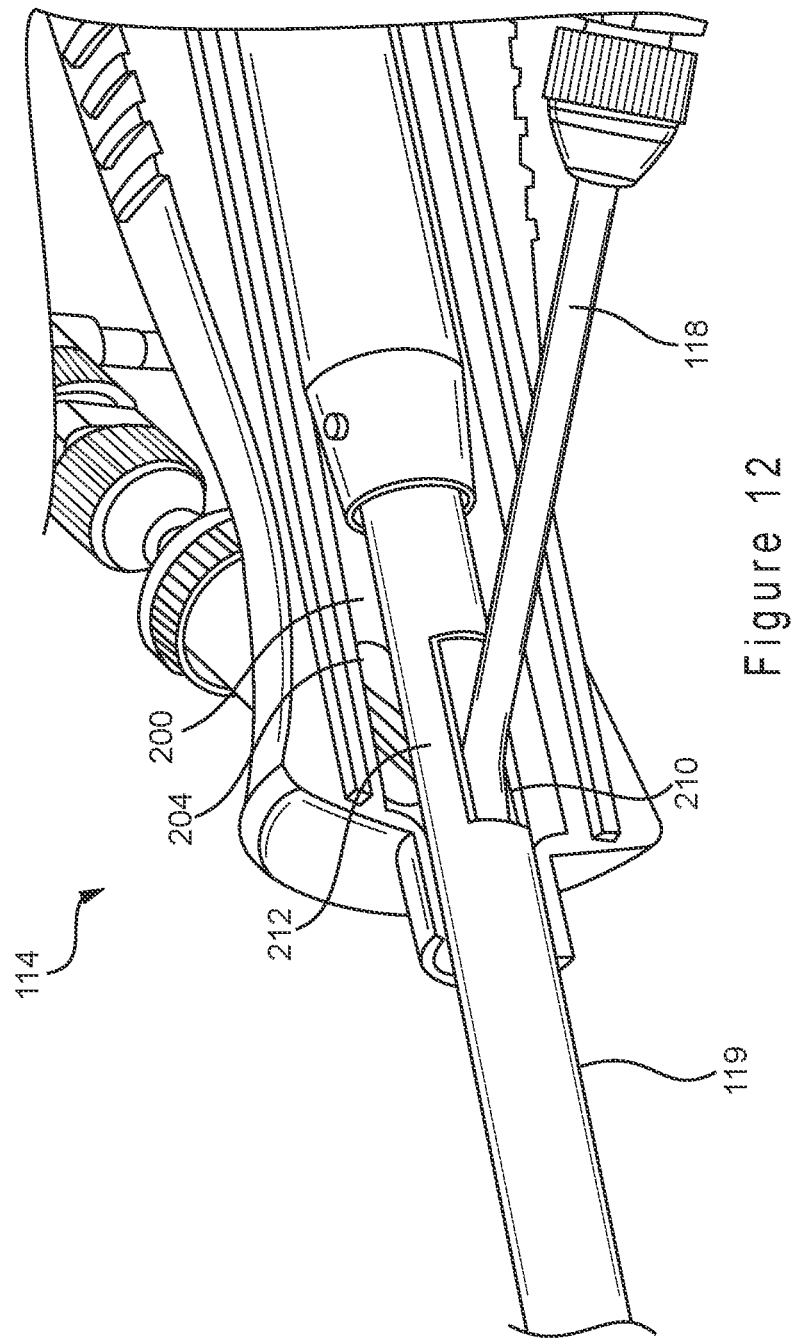
FIG. 12 shows a partial cross-sectional view of a handle portion of the embodiment of the stent graft delivery device of FIG. 1 with the auxiliary lumens extending therefrom.
Figure 13:
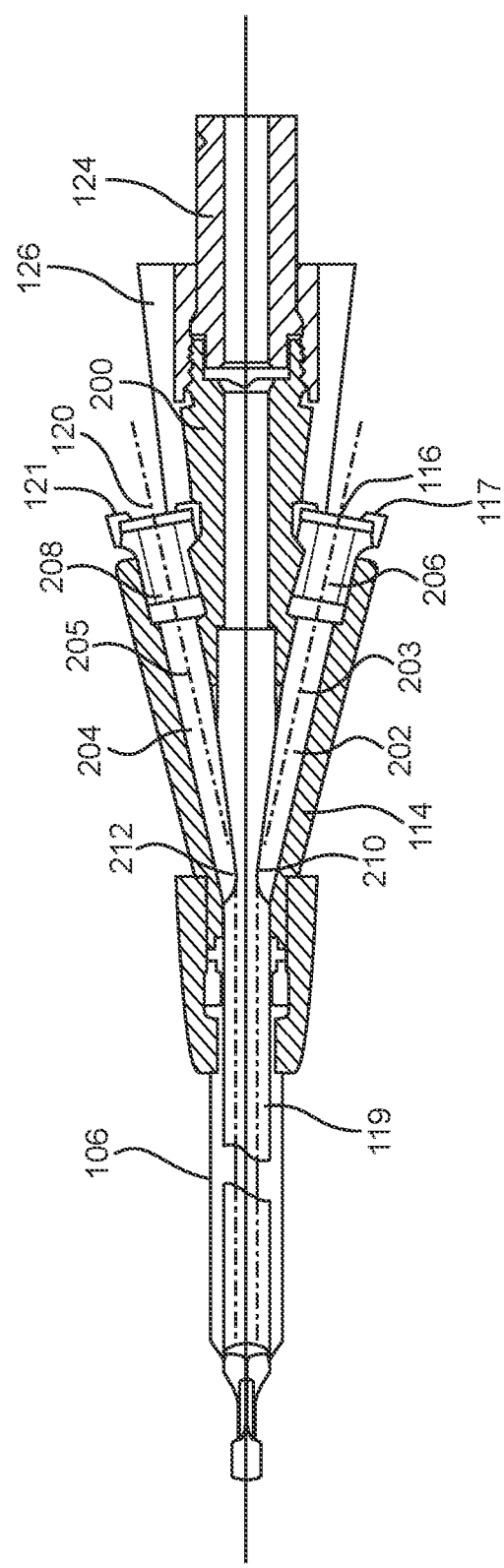
FIG. 13 shows a cross-sectional view of an assembly of a manifold and pusher chatter of the embodiment of the stent graft delivery device of FIG. 1.

The relationship between the manifold 114, the front handle 126, and the sheath 106 is shown in more detail in FIGS. 12 and 13. As shown in FIGS. 12 and 13, the manifold 114 forms part of the front handle 126 in this embodiment and includes a through bore 200 and angled side ports 202 and 204. As can be seen in FIGS. 11 and 12, the tri-lumen catheter 119 has two side apertures or windows 210 and 212 which open from the side of the tri-lumen catheter 119 into the respective lumens 92 and 94. These side apertures are elongate and tapered towards the distal end. When the tri-lumen catheter 119 is pushed into the through bore 200 of the manifold 114, the side apertures in the tri-lumen catheter 119 align with the respective angled side ports 202 and 204 of the manifold 114 thereby providing an uninterrupted lumen from the access port 116 for the first access sheath 118 into the pusher lumen 94 along the dotted line 203 and from access port 120 for a second access sheath 122 into the pusher lumen 92 along the dotted line 205 as shown in FIG. 10.

Figure 14D:
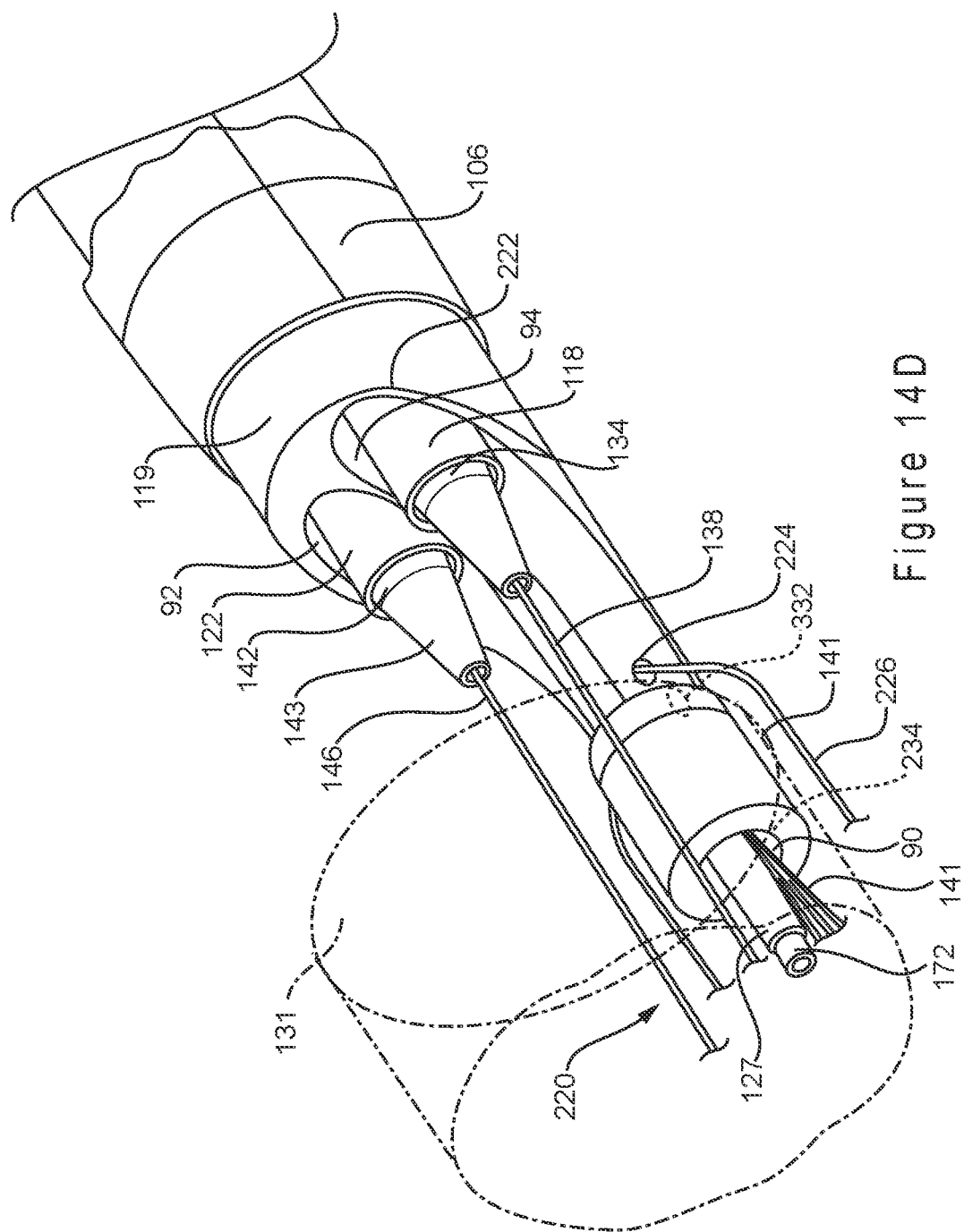

As can be best seen in FIGS. 14A to 14D, at the proximal end of the tri-lumen catheter 119 is an attachment boss 220 and a scalloped end 222 to provide exit ports for the two auxiliary lumens 92 and 94. The guide wire lumen 90 opens out at the proximal end of the attachment boss 220 and to each side of the attachment boss there are apertures for trigger wires. As shown in FIG. 14D, aperture 224 is for trigger wire 226 which is used for the diameter reducing ties on one side of the stent graft 131. A corresponding aperture 228 and the other side of the attachment boss 220 is for the trigger wire 230 for the other side of the stent graft 131. Trigger wire 141 extends out of aperture 232 in the attachment boss 220 and engages into the stent graft 131 before re-entering the attachment boss at aperture 234 and exiting the guide wire lumen 90 at the proximal end of the tri-lumen catheter 119. In one embodiment of the present invention, the access sheaths (or access sheaths) 118, 122 terminate out of the renal fenestrations on top of the graft material. The access sheaths 118,122 are preloaded through the graft fenestrations and are disposed within the manifold 114, which forms part of the front handle 126. Stent grafts for stenting side branches are preloaded in the access sheaths 118, 122 so as to allow for the cannulation of side branches after the main stent graft has been deployed at the desired location. The sheath 106 is disposed between the tri-lumen catheter 119 and the bore 200.

The stent graft delivery system 10 may introduced into the patient using the following steps:

1. Position the introduction part 104 of the delivery device 100 into the aorta correctly taking into account N-S position as well as rotational position with respect to target vessels and fenestrations 147 on the stent graft 131 using markers on stent graft body. At this stage the delivery device is as shown in FIGS. 1 and 2.

2. Withdraw the outer sheath 106 of the delivery device while continuing to check position until the distal end of the stent graft 131 opens. The splits 176 of the sheath 106 widen so as to allow the sheath 106 to be retracted relative to the first and second access sheaths 118, 122 without disturbing the location of the first and second access sheaths 118, 122. At this stage the distal end of the stent graft 131 is still retained by distal fixation, the proximal end is retained by the exposed stent retained in top capsule 111 of the delivery device 100 and the expansion of the stent graft 131 is restricted by the diameter reducing ties 227.

3. Position the access sheaths 118, 122 (left and right) on their respective indwelling guide wires 138,146 at the desired location within the lumen of stent graft 131 to or through the fenestration 147 (at this stage the top capsule 111 still retains the exposed stent 137 and the indwelling guide wires).

4. Position the first access sheath 118 at the opening of the fenestration 147.

5. Remove the dilator 134 of the first access sheath 118.

6. Advance buddy wire guide (4-5 Fr) disposed in the first access sheath into the target vessel (e.g. renal artery). The additional catheter may have a crooked, curled, hockey stick tip to facilitate access.

7. Release the stabilization retention system 250 of indwelling guide wires 138 via the proximal thumbhandle 164.

8. Remove the additional catheter and replace the access sheath dilator 134 and dilator catheter over the stiffer wire in the target vessel and advance the access sheath 118, 122 over the stiffer wire into the target vessel. Withdraw the access sheath dilator.

9. Repeat steps 4 to 9 for the other of the target vessels.

10. Release the top capsule 111 by removing the locking trigger wire 143 via the distal thumbwheel 166 of the rotational portion 162 of the trigger wire release assembly 159, releasing the pin vice 170 and advancing the top capsule 111 on the guide wire catheter 100 and release the top exposed stent 137. At the same time, the distally facing capsule moves proximally over the distal retrieval taper device 113 to allow the distal retrieval taper device 113 to extend from the distal end of the capsule 111. The ratchet assembly 190 prevents rotation of the distal thumbwheel in the clockwise direction, which further prevents and proximal motion of the locking trigger wire 143. The locking trigger wire 143 is wound about the spool 183 of the distal thumbwheel 166.

11. Tighten the pin vice 170.

12. Retract the nose cone dilator 110, top capsule 111 and distal retrieval taper 113 past the fenestration 147 by removing the set screw 174 to release the releasable portion 162 of the trigger wire release assembly 159 and moving the releaseable portion 162 in a distal direction. This also releases the distal attachment of the stent via trigger wire 141 connected to releasable portion 162. Retract the sheath 106 by rotating the back handle 128.

13. One at a time, withdraw the access sheaths 118, 122 from the target vessels and deploy covered stents between the fenestrations 147 and target vessels and balloon expand if necessary including flaring within the main stent graft 131.

14. Remove both access sheaths 118, 122 and also the guide wires from the target vessels and withdraw them from the system 100.

15. Retract the nose cone dilator 110, top capsule 111 and distal retrieval taper 113 to the sheath 106.

16. Withdraw the entire assembly 100. Further deployment may include a bifurcated distal component.

The introduction steps are also disclosed in U.S. Pat. No. 8,709,061, filed Jun. 6, 2011, entitled "Pre-loaded Multiport Delivery Device," the entirety of which is incorporated herein by reference in its entirety.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

The invention claimed is:

1. A preloaded stent graft delivery device, comprising:
a guidewire catheter having a proximal end, a distal end, and a guide wire lumen therethrough;
a nose cone dilator at the proximal end of the guidewire catheter, the nose cone dilator comprising a distal end and a capsule on the distal end of the nose cone dilator;
a handle assembly at the distal end of the guidewire catheter;
a trigger wire release assembly adjacent to the handle assembly comprising a first section and a second section releasably connected to the handle assembly and in communication with the capsule on the distal end of the nose cone dilator, the first section being rotatable about a longitudinal axis of the guidewire catheter, the first section of the trigger wire release assembly comprises one or more thumbhandles;
a trigger wire having a distal end and a proximal end, the proximal end being arranged to selectively couple the trigger wire release assembly to a prosthesis, the distal end of the trigger wire coupled to the first section of the trigger wire assembly;
a ratchet assembly disposed within an interior surface of the one or more thumbhandles of the first section of the trigger wire release assembly;
a pusher catheter extending from the handle assembly towards the nose cone dilator, the pusher catheter comprising at least one lumen therethrough where the guidewire catheter extends through the at least one lumen within the pusher catheter; and,
a sheath disposed coaxially over the pusher catheter, wherein the sheath has two longitudinal slits along a portion of a length of the sheath.

2. The preloaded stent graft delivery device of claim 1, wherein the pusher catheter further comprises two longitudinal auxiliary lumens.

3. The preloaded stent graft delivery device of claim 2, wherein the pusher catheter further comprises a proximal end spaced distally from the nose cone dilator and thereby defining a stent graft retention region between the proximal end of the pusher catheter and the nose cone dilator.

4. The preloaded stent graft delivery device of claim 3, further comprising a stent graft being releasably retained on the stent graft retention region.

5. The preloaded stent graft delivery device of claim 1, wherein the ratchet assembly comprises a ratchet surface and a pawl engaged with the ratchet surface.

6. The preloaded stent graft delivery device of claim 1, wherein the second section of the trigger wire release assembly is connected to the guidewire catheter via a pin vice.

7. The preloaded stent graft delivery device of claim 1, wherein a spool is positioned within the interior surface of the one or more thumbhandles of the first section.

8. The preloaded stent graft delivery device of claim 7, wherein the spool is positioned proximal to the ratchet assembly within the interior surface of the one or more thumbhandles of the first section.

9. A preloaded stent graft delivery device, comprising:
a guidewire catheter having a proximal end, a distal end, and a guide wire lumen therethrough;
a trigger wire release assembly at the distal end of the guidewire catheter, the trigger wire release assembly comprising a rotatable section, the rotatable section being rotatable about a longitudinal axis of the guidewire catheter and comprising one or more thumbhandles;
a ratchet assembly within an interior surface of the one or more thumbhandles of the rotatable section of the trigger wire release assembly;
a spool within the interior surface of the one or more thumbhandles of the rotatable section of the trigger wire release assembly, the spool positioned proximal to the ratchet assembly;
a trigger wire having a distal end and a proximal end, the proximal end being arranged to selectively couple the trigger wire release assembly to a prosthesis, the distal end of the trigger wire coupled to the spool within the interior surface of the one or more thumbhandles of the rotatable section of the trigger wire assembly; and,
a sheath at least partially disposed coaxially over the guidewire catheter.

10. The preloaded stent graft delivery device of claim 9, wherein the ratchet assembly comprises a ratchet surface and a pawl engaged with the ratchet surface.

11. The preloaded stent graft delivery device of claim 9 further comprising a releasable section connected to the trigger wire release assembly, the releasable section positioned distal to the rotatable section.

12. The preloaded stent graft delivery device of claim 9, wherein an outer diameter of the rotatable section is greater than an outer diameter of the spool.

13. A preloaded stent graft delivery device, comprising:
a guidewire catheter having a proximal end, a distal end, and a guide wire lumen therethrough;
a nose cone dilator at the proximal end of the guidewire catheter, the nose cone dilator comprising a distal end and a capsule on the distal end of the nose cone dilator;
a handle assembly at the distal end of the guidewire catheter;
a trigger wire release assembly at the distal end of the guidewire catheter, the trigger wire release assembly comprising a rotatable section and a releasable section distal to the rotatable section, the releasable section in communication with the capsule on the distal end of the nose cone dilator, the rotatable section being rotatable about a longitudinal axis of the guidewire catheter and comprising one or more thumbhandles;

a ratchet assembly disposed within an interior surface of the one or more thumbhandles of the rotatable section of the trigger wire release assembly, the ratchet assembly comprising a ratchet surface and a pawl engaged with the ratchet surface;

a spool within the interior surface of the one or more thumbhandles of the rotatable section of the trigger wire release assembly, the spool positioned proximal to the ratchet assembly;

a trigger wire having a distal end and a proximal end, the proximal end being arranged to selectively couple the trigger wire release assembly to a prosthesis, the distal end of the trigger wire coupled to the spool within the interior surface of the one or more thumbhandles of the rotatable section;

a pusher catheter extending from the handle assembly towards the nose cone dilator, the pusher catheter comprising at least one lumen therethrough where the guidewire catheter extends through the at least one lumen within the pusher catheter; and, a sheath disposed coaxially over the pusher catheter.

* * * * *